Figure 1:
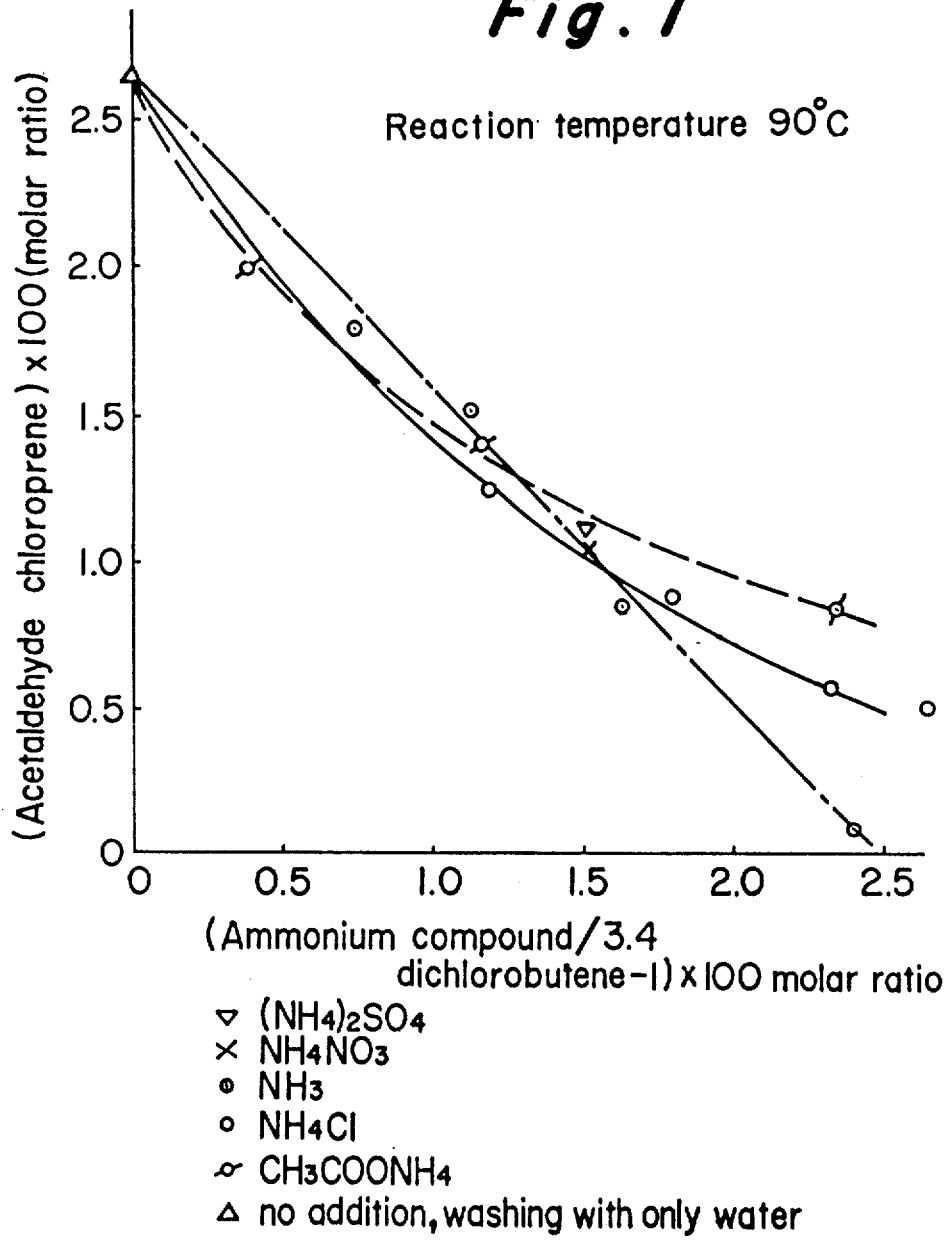

United States Patent [19]

Kadowaki et al.

[11] 4,130,596
[45] Dec. 19, 1978

[54] PROCESS FOR PRODUCING CHLOROPRENE MONOMER HAVING A LITTLE CONTENT OF ACETALDEHYDE

[75] Inventors: Takashi Kadowaki; Michio Nishimura; Seiichi Watanabe; Koichi Abe, all of Ohmi, Japan

[73] Assignee: Denki Kagaku Kogyo Kabushiki Kaisha, Tokyo, Japan

[21] Appl. No.: 543,107

[22] Filed: Jan. 22, 1975

Related U.S. Application Data

[63] Continuation of Ser. No. 21,740, Mar. 23, 1970, abandoned.

[30] Foreign Application Priority Data

Mar. 24, 1969 [JP] Japan .................................. 44-21900
Apr. 21, 1969 [JP] Japan .................................. 44-30375

[51] Int. Cl.² .............................................. C07C 21/20
[52] U.S. Cl. .................................................... 260/655
[58] Field of Search ............... 260/655, 654 D, 654 S, 260/21, 740

[56] References Cited

U.S. PATENT DOCUMENTS

2,361,072  10/1944  Vining ............................ 260/654 D
2,430,016  11/1947  Hearne et al. ....................... 260/655

Primary Examiner—Delbert E. Gantz
Assistant Examiner—Joseph A. Boska
Attorney, Agent, or Firm—Sughrue, Rothwell, Mion, Zinn and Macpeak

[57] ABSTRACT

Chloroprene having a little content of acetaldehyde is produced by dehydrochlorination of 3,4-dichlorobutene-1 in the presence of an aqueous solution of an alkali metal hydroxide by treating with an ammonium ion donor during or after the dehydrochlorination or in both the steps.

12 Claims, 2 Drawing Figures

PROCESS FOR PRODUCING CHLOROPRENE MONOMER HAVING A LITTLE CONTENT OF ACETALDEHYDE

This is a continuation, of application Ser. No. 21,740, filed Mar. 23, 1970, now abandoned.

The present invention relates to new production process of chloroprene monomer having a little content of acetaldehyde and more particularly to production of chloroprene having a small amount of acetaldehyde wherein when 3,4-dichlorobutene-1 is dehydrochlorinated in the presence of an alkali metal hydroxide to produce chloroprene, the reaction mixture or the reaction product is treated with an ammonium ion donor.

It has been well known to produce chloroprene by dehydrochlorinating 3,4-dichlorobutene-1 in the presence of an aqueous solution of an alkali metal hydroxide. In this case acetaldehyde is by-produced and the by-produced amount depends upon the reaction conditions, particularly upon the reaction temperature. When the reaction is effected at 80° to 100° C., the amount of acetaldehyde by-produced is 1.0 to 3.0 mol%, 0.5 to 1.5% by weight based on the resulting chloroprene.

Acetaldehyde in chloroprene monomer is injurious to the properties of polychloroprene therefrom. Accordingly, it is generally required to decrease the concentration of acetaldehyde in chloroprene monomer to less than 0.4 mol% (0.2% by weight). As a method for separating acetaldehyde from chloroprene monomer, extraction process by water has been known.

However, according to this process it is necessary to use a relatively large amount of water and a relatively long contact time in order to extract acetaldehyde to the tolerable concentration of 0.2% by weight. Chloroprene being easily polymerized by the action of water or oxygen dissolved in water, a long contact time may cause an undesirable polymerization. For example, when the extraction is effected in a packed column by a counter current of water, pop corn-like polymer may be formed and lead to frequent operation obstruction. Accordingly it has been desired to improve this process.

The inventors have found that ammonium ion is effective for decreasing the acetaldehyde by-produced and for removing acetaldehyde by-produced when 3,4-dichlorobutene-1 is dehydrochlorinated by means of an aqueous solution of an alkali metal hydroxide to produce chloroprene.

An object of the present invention is to decrease the acetaldehyde by-produced in production of chloroprene by dehydrochlorination of 3,4-dichlorobutene-1 by using an aqueous solution of an alkali metal hydroxide.

The other object of the present invention is to remove effectively acetaldehyde contained in chloroprene.

In addition, the present invention provides a method of producing chloroprene having a little content of acetaldehyde which is suitable for the starting monomer to be used for polymerization of chloroprene, by attaining these objects. The inventors have found that chloroprene having a little content of acetaldehyde can be produced by the treatment with an ammonium ion donor in or after the dehydrochlorination reaction of 3,4-dichlorobutene-1 by means of an alkali metal hydroxide.

Namely, the inventors have ascertained that when 3,4-dichlorobutene-1 is dehydrochlorinated in the presence of an aqueous solution of an alkali metal hydroxide to produce chloroprene, it is possible to decrease the by-production of acetaldehyde by adding ammonium ion donor to the reaction mixture or it is possible to remove the by-produced acetaldehyde in chloroprene by extracting the resulting chloroprene with an aqueous solution of an ammonium ion donor.

The present invention will be explained in more detail.

Figure 2:
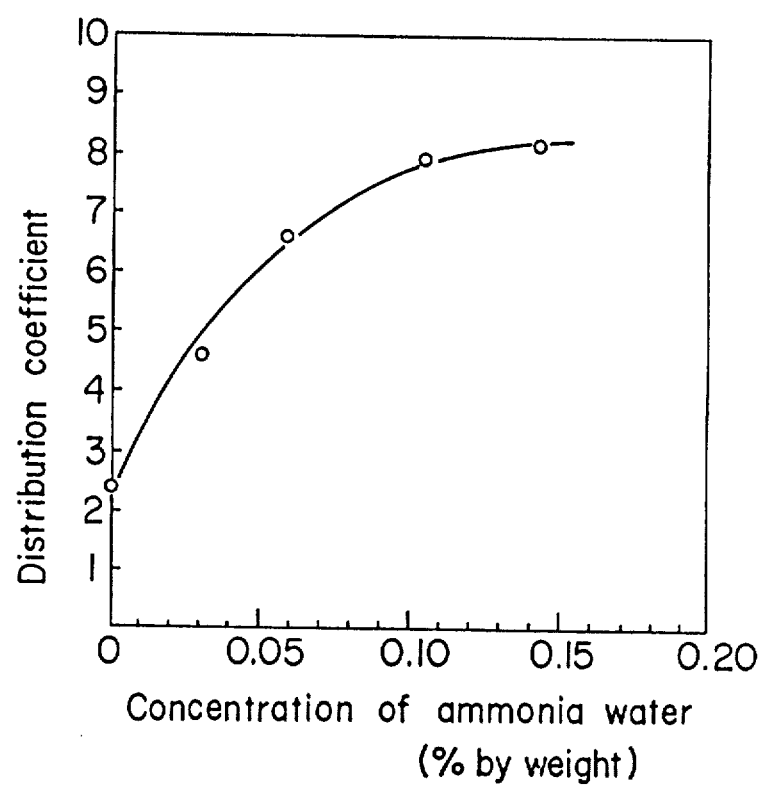

For a better understanding of the invention, reference is taken to the accompanying drawings, wherein:

FIG. 1 is curves showing the relation of amounts of ammonium ion donors added and amounts of acetaldehyde by-produced; and FIG. 2 is a curve showing the relation of concentrations of ammonia water to distribution coefficient when acetaldehyde contained in chloroprene as an impurity is extracted by a diluted ammonia water having various concentrations.

As ammonium ion donors to be added in the production of chloroprene through dehydrochlorination in the presence of an aqueous solution of an alkali metal hydroxide, for example, use may be made of ammonia, ammonium chloride, ammonium nitrate, ammonium sulfate, ammonium acetate and the like.

The ammonium ion donors may be added continuously to the reaction mixture as an aqueous solution. The amount of acetaldehyde by-produced decreases as the amount of ammonium ion donor added increases.

As mentioned above, FIG. 1 is curves showing the relation of the amount of ammonia, ammonium chloride, ammonium acetate, ammonium sulfate, and ammonium nitrate added based on 3,4-dichlorobutene-1 to the amount of acetaldehyde by-produced in chloroprene at the reaction temperature of 90° C.

As shown in FIG. 1, the effect of decreasing the acetaldehyde by-produced varies depending upon the amount and sort of the ammonium ion donor but the donor has apparently a much higher effect than the case of the water alone extraction. The amount of the ammonium ion donor to be added is determined by the reaction condition, tolerance amount of acetaldehyde in chloroprene monomer and kind of ammonium ion donor.

According to the present invention, the amount of acetaldehyde by-produced during the production of chloroprene can be considerably decreased by continuously adding an ammonium ion donor to the reaction mixture, and therefore the resulting chloroprene may be used directly as a starting material for polymerization without removing acetaldehyde after the dehydrochlorination reaction.

However, even when the dehydrochlorination reaction is effected according to the method of the present invention, a small amount of acetaldehyde may be by-produced. Such an amount of acetaldehyde may not cause serious problems in general, but it must be sometimes removed, if necessary.

The inventors have found that when acetaldehyde is extracted from chloroprene with an aqueous solution of ammonium ion donor, the content of acetaldehyde in the chloroprene can be further decreased than the conventional extraction method with water. As the aqueous solution of ammonium ion donor, ammonia water is preferable.

The concentration of ammonia water to be used in the present invention is sufficient in the range of 0.01–0.15% by weight, and in such concentration, the distribution coefficient is considerably higher than the case where pure water is used. This surprising effect is one of the advantages of the present invention. FIG. 2 shows the distribution coefficient of acetaldehyde at 10° C. in ammonia water-chloroprene system. The term "distribution coefficient" used herein means a value obtained by dividing the number of grams of solute in 100g of extract layer by the number of grams of solute in 100g of raffinate layer. It will be apparent from FIG. 2 that ammonia water is an excellent extracting agent.

In the present invention, the extraction can be effected at a temperature of 0°-25° C. However, the temperature is preferred to be 0°-10° C. in order to prevent chloroprene from formation of undesirable polymerization product. Further, a suitable polymerization inhibitor may be used, if necessary.

The ratio of chloroprene containing acetaldehyde impurity to the extracting agent (ammonia water having the concentration as described above) varies depending upon the type of extraction procedure, but it is preferred to be 2-0.5 (weight ratio).

This ratio should be selected so as to be most economic considering the type of extraction procedure and other factors.

The mutual solubility and the difference of densities between ammonia water and chloroprene to be used in the present invention are substantially the same with those between pure water and chloroprene at a concentration range of ammonia water of 0.01-0.15% by weight, and consequently the losses of the chloroprene and the extracting agent are very small as in the case when water is used as an extracting agent, and the separation can be easily effected by settling.

The chloroprene to be used in the extraction of the present invention may include one prepared by adding or not adding an ammonium ion donor at the dehydrochlorination process of 3,4-dichlorobutene-1.

A preferable embodiment of the present invention will be explained as follows:

Into a reactor equipped with a stirrer, a thermometer, a condenser, an inlet for raw material and a discharging opening for aqueous phase of reaction mixture are charged 3,4-dichlorobutene-1, aqueous solution of sodium hydroxide, and ammonia water, and the resulting mixture is reacted at a predetermined temperature. Gaseous reaction product from the reactor is introduced into an extractor through the condenser. Ammonia water is further charged into the extractor. Aldehyde contained in the resulting chloroprene is extracted with the ammonia water, and then an organic phase and a water phase are separated. The thus obtained organic phase consists mainly of chloroprene, unreacted dichlorobutene and by-produced 1-chlorobutadiene, and contains very small amount of aldehyde.

The following examples are given in illustration of this invention and are not intended as limitations thereof.

EXAMPLE 1

Into a reactor equipped with a stirrer, a thermometer, a condenser, an inlet for raw material and a discharging opening for aqueous phase of reaction mixture (NaCl + NaOH) were charged 90 parts by volume of 5% aqueous solution of sodium hydroxide and 10 parts by volume of 3,4-dichlorobutene-1 (hereinafter abbreviated as 3,4-DCB-1). Then, the reactor was charged continuously with 5% aqueous solution of sodium hydroxide, 3,4-DCB-1 and ammonia water having a concentration of 1.5% by weight in amounts of 70, 10 and 3 parts by volume per unit time respectively, while keeping the reaction mixture at a temperature of 90° C. Liquid and vapor from the condenser were collected in a bottle kept at 5° C. The reaction product collected after the reaction reached stationary state was separated into an organic phase and an aqueous phase, and the organic phase was analyzed by means of gas chromatography. Furthermore, with respect to a part of the organic phase, aldehyde was analyzed by the iodometry using sodium bisulfite. Aldehyde contained in the aqueous phase of the reaction product was analyzed by the above-mentioned method. The aldehyde was identified to be acetaldehyde by means of gas chromatography and infrared absorption spectrum. It was confirmed that the result obtained by the gas chromatography analysis agreed quantitatively with that obtained by the above chemical analysis within the range of experimental error. The amount of acetaldehyde by-produced in the reaction product, that is, the total amount of acetaldehyde in the aqueous phase and the organic phase, was 0.84 mol% based on chloroprene (hereinafter abbreviated as CP). Acetaldehyde was not contained in the aqueous solution of unreacted sodium hydroxide taken out from the reactor.

By varying the amount of ammonia water added, the tests as mentioned above were repeated to obtain a result as shown in the following Table 1 and by the mark (⊙) in FIG. 1.

Table 1

| Amount of ammonia added (molar ratio of NH₃/3,4-DCB-1) | Amount of acetaldehyde by-produced (molar ratio of CH₃CHO/CP) |
| --- | --- |
| 0 | 0.0276 |
| 0.0076 | 0.0179 |
| 0.0114 | 0.0151 |
| 0.0164 | 0.0084 |
| 0.0240 | 0.0008 |

As shown in the above result, the amount of acetaldehyde by-produced was considerably decreased by the addition of ammonia.

EXAMPLE 2

A series of experiments was effected in the same manner as described in Example 1, except that ammonium chloride was used instead of ammonia, to obtain a result as shown in the following Table 2 and by the mark (o) in FIG. 1.

Table 2

| Amount of ammonium chloride added (molar ratio of NH₄Cl/3,4-DCB-1) | Amount of acetaldehyde by-produced (molar ratio of CH₃CHO/CP) |
| --- | --- |
| 0 | 0.0276 |
| 0.0120 | 0.0124 |
| 0.0183 | 0.0086 |
| 0.0234 | 0.0056 |
| 0.0267 | 0.0050 |

As shown in the above result, the amount of acetaldehyde by-produced was considerably decreased by the addition of ammonium chloride.

EXAMPLE 3

A series of experiments was effected in the same manner as described in Example 1, except that ammonium acetate was used instead of ammonia, to obtain a result as shown in the following Table 3 and by the mark (□) in FIG. 1.

Table 3

| Amount of ammonium acetate added (molar ratio of CH₃COONH₄/3,4-DCB-1) | Amount of acetaldehyde by-produced (molar ratio of CH₃CHO/CP) |
|---|---|
| 0 | 0.0276 |
| 0.0046 | 0.0201 |
| 0.0118 | 0.0139 |
| 0.0236 | 0.0082 |

As shown in the above result, the amount of acetaldehyde by-produced was considerably decreased by the addition of ammonium acetate.

EXAMPLE 4

An experiment was effected in the same manner as described in Example 1, except that ammonium nitrate was used instead of ammonia in a molar ratio of ammonium nitrate to 3,4-DCB-1 of 0.0150. The amount of acetaldehyde by-produced was 0.0105 in the molar ratio based on chloroprene. The result is shown by the mark (x) in FIG. 1.

EXAMPLE 5

An experiment was effected in the same manner as described in Example 1, except that ammonium sulfate was used instead of ammonia in a molar ratio of ammonium sulfate to 3,4-DCB-1 of 0.0150. The amount of acetaldehyde by-produced was 0.0113 in the molar ratio based on chloroprene. The result is shown by the mark (∇) in FIG. 1.

EXAMPLE 6

A flask equipped with a stirrer was placed in a thermostat kept at 10° C. Into the flask were charged 50 parts by weight of chloroprene containing 1.24% by weight of acetaldehyde and 50 parts by weight of ammonia water having a concentration as shown in the following Table 4. After stirring vigorously for 20 minutes, the reaction mixture was introduced into a separating funnel and left to stand for 1 hour. The organic phase and the aqueous phase were separated, and each phase was analyzed in the following method to determine the concentration of acetaldehyde contained in each phase. The analysis of acetaldehyde was effected by the iodometry using sodium bisulfite, but it had been confirmed prior to the iodometry that ammonia did not disturb this analysis. It was confirmed that in Examples 6 to 8 the material balance of acetaldehyde before and after the extraction coincided completely within the range of experimental error. The obtained result in this Example 6 is shown in the following Table 4.

Table 4

| Concentration of ammonia water (% by weight) | Distribution coefficient |
|---|---|
| 0 | 2.41 |
| 0.030 | 4.60 |
| 0.058 | 6.63 |
| 0.104 | 7.98 |
| 0.143 | 8.35 |

As shown in Table 4, the distribution coefficient in the use of ammonia water is considerably higher than that in the use of pure water, and as the concentration of ammonia water increases, the distribution coefficient increases and reaches maximum value at the concentration of 0.15% by weight of ammonia water. The numerical values in Table 4 were plotted to obtain a curve in FIG. 2, by which the above-mentioned tendency will be understood more clearly.

In the practice of the method of the present invention, even if chloroprene contains impurities other than acetaldehyde, these impurities do not influence the present invention at all. This will be explained in the following Examples 7 and 8.

EXAMPLE 7

A series of experiments was effected in the same manner as described in Example 6, except that chloroprene containing 2.5% by weight of 1-chlorobutadiene-1,3 and 1.32% by weight of acetaldehyde was used as a raw material, to obtain a result as shown in the following Table 5.

Table 5

| Concentration of ammonia water (% by weight) | Distribution coefficient |
|---|---|
| 0 | 2.38 |
| 0.026 | 4.45 |
| 0.053 | 5.93 |
| 0.11 | 8.05 |
| 0.15 | 8.30 |

As shown in Table 5, even when chloroprene contains a small amount of 1-chlorobutadiene-1,3 in addition to acetaldehyde, such 1-chlorobutadiene-1,3 does not substantially influence on the extraction effect.

EXAMPLE 8

A series of experiments was effected in the same manner as described in Example 6, except that a mixture of 48.2% by weight of 3,4-DCB-1, 1.2% by weight of 1-chlorobutadiene-1,3, 0.61% by weight of acetaldehyde and 50% by weight of chloroprene was used as a raw material, to obtain a result as shown in the following Table 6.

Table 6

| Concentration of ammonia water (% by weight) | Distribution coefficient |
|---|---|
| 0 | 1.24 |
| 2.90 | 3.15 |
| 5.85 | 4.80 |
| 1.07 | 6.43 |
| 1.39 | 6.50 |

Table 6 shows that the method of the present invention is not influenced at all even in the presence of a relatively large amount of 3,4-DCB-1. Because, although the distribution coefficient shown in Table 6 is lower than those shown in Tables 4 and 5 as a whole, ammonia water has a distribution coefficient considerably higher than pure water.

EXAMPLE 9

Into a reactor equipped with a stirrer, a thermometer, a condenser, an inlet for raw material and a discharging opening for aqueous phase reaction mixture (NaCl + NaOH) were charged 90 parts by volume of 5% aqueous solution of sodium hydroxide and 10 parts by volume of 3,4-DCB-1. Then, the reactor was charged continuously with 5% aqueous solution of sodium hydroxide, 3,4-DCB-1 and ammonia water having a concentration of 1.5% by weight in amounts of 70, 10 and 3 parts by volume per unit time respectively, while keeping the reaction mixture at a temperature of 90° C. Liquid and vapor from the condenser were collected in a bottle kept at 5° C. The collected reaction product was introduced into an extractor equipped with a stirrer. Ammonia water having a concentration of 1.5% by weight was introduced into the extractor at a rate of 10 parts by volume per unit time. The extract was then introduced into a tank, in which an organic phase and a water phase were separated. The organic phase was analyzed by means of gas chromatography, and further aldehyde in the organic phase was analyzed. The obtained result is shown in the following Table 7.

Table 7

| CP (% by weight) | 3,4-DCB-1 (% by weight) | 1-chloro-butadiene-1,3 (% by weight) | Aldehyde (% by weight) |
|---|---|---|---|
| 47.6 | 51.1 | 1.2 | 0.0002 |

What is claimed is:

1. A method for producing chloroprene which comprises:
   dehydrochlorinating 3,4-dichlorobutene-1 with an aqueous solution of an alkali metal hydroxide in the presence of an ammonium ion donor chosen from the group consisting of ammonium acetate, ammonium nitrate and ammonium sulfate, said ammonium ion donor being present in an amount of from 0.5 mol % to 2.5 mol % based on 3,4-dichlorobutene-1.

2. The method of claim 1, wherein said ammonium ion donor is ammonium acetate.

3. The method of claim 1, wherein the ammonium ion donor is ammonium nitrate.

4. The method of claim 1, wherein the ammonium ion donor is ammonium sulfate.

5. A method for producing chloroprene which comprises:
   dehydrochlorinating 3,4-dichlorobutene-1 with an aqueous solution of an alkali metal hydroxide in the presence of an ammonium ion donor chosen from the group consisting of ammonium acetate, ammonium nitrate and ammonium sulfate, said ammonium ion donor being present in an amount of from 0.5 mol % to 2.5 mol % based on 3,4-dichlorobutene-1 to produce chloroprene, and subsequently extracting acetaldehyde contained in said chloroprene with ammonia water.

6. The method of claim 5, wherein the ammonium ion donor is ammonium acetate.

7. The method of claim 5, wherein the ammonium ion donor is ammonium nitrate.

8. The method of claim 5, wherein the ammonium ion donor is ammonium sulfate.

9. A method of producing chloroprene which comprises:
   dehydrochlorinating 3,4-dichlorobutene-1 with an aqueous solution of an alkali metal hydroxide in the presence of an ammonium ion donor chosen from the group consisting of ammonium acetate, ammonium nitrate and ammonium sulfate, said ammonium ion donor being present in an amount from 0.5 mol % to 2.5 mol % based on 3,4-dichlorobutene-1 to produce chloroprene, and
   subsequently extracting acetaldehyde contained in said chloroprene with an aqueous solution of an ammonium ion donor chosen from the group consisting of ammonium water, ammonium chloride ammonium acetate, ammonium nitrate and ammonium sulfate.

10. The method of claim 9, wherein the ammonium ion donor in the dehydrochlorinating step is ammonium acetate.

11. The method of claim 9, wherein the ammonium ion donor in the dehydrochlorinating step is ammonium nitrate.

12. The method of claim 9, wherein the ammonium ion donor in the dehydrochlorinating step is ammonium sulfate.

* * * * *